United States Patent
Kimler

(10) Patent No.: US 6,869,613 B2
(45) Date of Patent: Mar. 22, 2005

(54) SPRAYABLE INSECTICIDAL COMPOSITIONS HAVING ENHANCED EFFICACY

(75) Inventor: Joseph Kimler, Yardville, NJ (US)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/282,857

(22) Filed: Mar. 31, 1999

(65) Prior Publication Data

US 2002/0054898 A1 May 9, 2002

Related U.S. Application Data

(60) Provisional application No. 60/080,117, filed on Mar. 31, 1998.
(51) Int. Cl.⁷ ................................. A01N 25/26
(52) U.S. Cl. ...................... 424/421; 424/45; 424/46; 424/405; 424/406
(58) Field of Search ................... 424/45, 405, 406, 424/409, 417, 421, 46; 514/919, 427, 428; 428/403, 404

(56) References Cited

U.S. PATENT DOCUMENTS

| | | |
|---|---|---|
| 4,678,774 A | 7/1987 | Putter et al. |
| 5,118,816 A | 6/1992 | Doehner et al. |
| 5,187,184 A | 2/1993 | Lovell |
| 5,310,938 A | 5/1994 | Brown et al. |
| 5,496,845 A | 3/1996 | Martin et al. |

FOREIGN PATENT DOCUMENTS

| | | | |
|---|---|---|---|
| EP | 0304492 | * | 9/1988 |
| WO | WO 97 12516 A | | 4/1997 |

* cited by examiner

*Primary Examiner*—Neil S. Levy
(74) *Attorney, Agent, or Firm*—Novak, Druce, DeLuca & Quigg

(57) ABSTRACT

There is provided a sprayable insecticidal composition having significantly increased efficacy which comprises an effective amount of an insecticide; an abrasive; a low level of a surfactant; an inert carrier; and optionally a film-forming inhibitor.

17 Claims, No Drawings

SPRAYABLE INSECTICIDAL COMPOSITIONS HAVING ENHANCED EFFICACY

This application claims the benefit of provisional application 60/080,117 filed on Mar. 31, 1998.

BACKGROUND OF THE INVENTION

Control of cockroaches and other crawling insects is traditionally achieved by applying sprayable insecticidal formulations, diluted with water, to various microhabitats within the infested premises. In the control of crawling insect pests such as German cockroaches, which typically inhabit kitchens, food preparation areas and similar sites, these insecticidal formulations must be applied to a wide variety of substrates found in homes and commercial establishments. Many of these substrates, such as particle board or related composites, vinyl tiles or painted finishes, are highly porous, permitting the insecticidal formulation to be absorbed into the substrate where the active agent may become unavailable and fail to control the target insect pest.

Sprayable formulations such as emulsifiable concentrates, are widely known to readily penetrate porous substrates thereby becoming unavailable on the surface of porous substrates. Conventional suspension concentrate compositions of insecticides such as arylpyrroles, particularly chlorfenapyr are described e.g. in U.S. Pat. No. 5,496,845.

It is an object of this invention to provide sprayable insecticidal compositions having increased efficacy, particularly when applied to the surfaces of a variety of substrates found in homes, warehouses, commercial establishments and the like.

SUMMARY OF THE INVENTION

It has now been found that a sprayable insecticidal composition which produces an abrasive, dislodgeable film or residue after spraying and drying, significantly enhances the efficacy of said insecticidal composition, particularly when applied to the surfaces of a variety of substrates found in homes, warehouses, commercial establishments and the like.

The present invention provides a sprayable insecticidal composition which comprises an insecticidally effective amount of an insecticide; an abrasive; a low level of surfactant; an inert carrier; and optionally a film-forming inhibitor. The composition of the invention provides superior control of crawling insect pests when applied to the surface of a variety of substrates found in homes, warehouses, commercial establishments and the like.

DETAILED DESCRIPTION OF THE INVENTION

Insecticides such as the arylpyrroles described in U.S. Pat. No. 5,310,938 are potent contact insecticides as well as highly potent insect stomach poisons and very efficacious when ingested by the target pestiferous insect. In crop protection practice, sprayable insecticidal compositions are effective in general because the target insect pest, in addition to directly contacting residues, ingests the insecticide while consuming the treated plant. However, surprisingly compositions of the present invention demonstrate increased efficacy in structural pest control practice over the conventional sprayable suspension concentrate composition of arylpyrrole insecticides.

Surprisingly, it has now been found that a sprayable insecticidal composition comprising an effective amount of an insecticide, such as an arylpyrrole insecticide, an abrasive, a low surfactant level, an inert carrier and optionally a film-forming inhibitor demonstrates a significantly enhanced efficacy against crawling insect pests such as cockroaches, ants, crickets, silverfish, earwigs, flour beetles, termites, wood-boring beetles and the like. The composition of the invention forms a dislodgeable, abrasive residue which attaches to, and irritates, the crawling insect pest as it passes through, or travels over, the treated surface. This adherence of the insecticidal residue promotes direct cuticular absorption of insecticide and, most significantly, indirectly ingestion as a result of the target insect pest grooming body parts such as antennae or tarsi in order to become free of the residual deposits. Advantageously, the composition of the invention demonstrates a superior effect to that of the conventional sprayable suspension concentrate insecticidal composition.

Among the insecticides suitable for use in the inventive composition are any known insecticides useful for the control of crawling insects, preferably arylpyrrole insecticides, particularly chlorfenapyr. In actual practice insecticidally effective amounts may depend upon a variety of factors known to one of ordinary skill in the art e.g. potency of the active ingredient; typically the amount may be on a wt/wt basis about 10%–70%, preferably 10%–30%.

Abrasives suitable for use in the inventive composition may be silicate salts, such as an alkaline earth metal silicate or alkali metal silicate (preferably calcium silicate), or silica or kaolin clay or a mixture thereof, preferably calcium silicate or kaolin clay or a mixture thereof, more preferably calcium silicate. The abrasive may suitably be present on a wt/wt basis of about 3%–9%, preferably about 5%–7%.

Surfactants suitable for use in the composition of the invention may be any known surface-active agent, wetting agent, dispersant, or a mixture thereof. A surface-active agent may be an emulsifying agent, a dispersing agent or a wetting agent; it may be non-ionic or ionic. Examples of suitable surface-active agents include the sodium or calcium salts of polyacrylic acids and lignin sulphonic acids; formaldehyde condensates of alkylated napthalene sulphonates such as MORWET® D425; Dioctyl sodium sulphosuccinate; the condensation products of fatty acids of aliphatic amines or amides containing at least 12 carbon atoms in the molecule with ethylene oxide and/or propylene oxide; fatty acid esters of glycol, sorbitan, sucrose or pentaerythritol; condensates of these with ethylene oxide and/or propylene oxide; condensation products of fatty alcohol or alkyl phenols, for example p-octylphenol or p-octylcresol, with ethylene oxide and/or propylene oxide; sulphates or sulphonates of these condensation products; alkali or alkaline earth metal salts, preferably sodium salts, of sulphuric of sulphonic acid esters containing at least 10 carbon atoms in the molecule, for example sodium lauryl sulphate, sodium secondary alkyl sulphates, sodium salts of sulphonated castor oil, and sodium alkaryl sulphonates such as dodecylbenzene sulphonate; and polymers of ethylene oxide and copolymers of ethylene oxide and propylene oxide. Preferred surfactants include formaldehyde condensates of alkylated napthalene sulphonates and dioctyl sodium sulphosuccinate. In actual practice, the level of surfactant may be higher in the presence of a film-forming inhibitor, than in the absence of said inhibitor. Suitable levels of a surfactant (in the absence of said inhibitor) on a wt/wt basis are levels below 8%, such as 2%–7%, preferably 3%–5%. In the absence of a film-forming inhibitor levels of surfactant below 8% are referred to herein as "low levels" of surfactant. In the presence of said film-forming inhibitor levels of surfactant may range as high as 15%, preferably 8% to 12% and are still considered "low levels" of surfactant herein. Compositions comprising a film-forming inhibitor and having less than about 8% surfactant are especially preferred.

The inert carrier suitable for use in the inventive composition may be any agriculturally acceptable solid or liquid carrier, preferably a solid carrier. Suitable solid carriers include natural and synthetic clays and silicates, for example natural silicas such as diatomaceous earths; magnesium silicates, for example talcs; magnesium aluminum silicates, for example attapulgites and vermiculites; aluminum silicates, for example kaolinites, montmorillonites and micas; calcium carbonate; calcium sulphate; ammonium sulphate; synthetic hydrated silicon oxides and synthetic calcium or aluminum silicates; elements, for example carbon and sulphur; natural and synthetic resins, for example coumarone resins, polyvinyl chloride, and styrene polymers and copolymers. Preferable solid carriers are kaolin clay, diatomaceous earth, montmorillonite clay, and the like, more preferably kaolin clay. In actual practice, the inert carrier may be present in the inventive composition on a wt/wt basis at about 25%–75%, preferably about 55%–65%.

The optional film-forming inhibitor suitable for use in the inventive composition may be any inert particulate material useful for the inhibition of the formation of a continuous film residue after the composition has been sprayed and dried. Particularly useful are inorganic salts such as alkali metal halides or alkaline earth metal halides, preferably alkaline earth metal halides such as calcium chloride. The presence of an inorganic salt in the composition prohibits the formation of an uninterrupted film upon the drying of the composition residue. However, if the surfactant level of the composition is sufficiently low, the film-forming inhibitor is not required to obtain a dislodgeable residue. In actual practice, if present, the film-forming inhibitor is typically present on a wt/wt basis at about 1%–6%, preferably about 2%–4%.

The sprayable insecticidal compositions of the invention may be prepared by admixing an effective amount of an insecticide such as chlorfenapyr, an abrasive such as a silicate salt, silica, kaolin clay or a mixture thereof, preferably a silicate salt such as calcium silicate, a low level of a surfactant such as an amount of less than 8% wt/wt, an inert carrier such as kaolin clay and optionally a film-forming inhibitor such as an inorganic salt and milling the mixture until homogeneous. It is important that a sprayable insecticidal formulation demonstrate minimal absorption so as to maximize the availability of an effective dose of the insecticide as the insect passes over or through treated areas.

The invention also provides for a method to control crawling insects comprising spraying in the locus of said crawling insects an effective amount of a composition of the invention. The locus of the crawling insect includes the insect and anywhere where the insect may crawl including, but not limited to, its habitat, breeding area, or food supply.

For a more clear understanding of the invention, the following examples are set forth below. These examples are merely illustrative and are not understood to limit the scope or underlying principles of the invention in any way.

Unless otherwise noted, all parts are parts by weight.

EXAMPLE 1

Evaluation of the Enhanced Efficacy of a Sprayable Insecticidal Composition Containing an Abrasive The wettable powder compositions shown in Table I are prepared by combining all ingredients and milling until homogeneous.

TABLE I

| | wt/wt % | | | | | | |
|---|---|---|---|---|---|---|---|
| Ingredient | A | B | C | D | E | F | G |
| Chlorfenapyr | 72.0 | 56.6 | 41.1 | 25.7 | 25.2 | 24.8 | 24.8 |
| Wetting Agent[1] | 2.5 | 2.5 | 2.5 | 2.5 | 2.5 | 2.5 | 2.5 |
| Dispersing Agent[2] | 4.5 | 4.5 | 4.5 | 4.5 | 4.5 | 17.5 | 4.5 |
| Calcium Chloride | 1.0 | 1.0 | 1.0 | 1.0 | 1.0 | 1.0 | 1.0 |
| Calcium Silicate | — | — | — | — | 2.0 | — | — |
| Kaolin Clay | 20.0 | 35.4 | 50.9 | 66.3 | 64.8 | 54.2 | 67.2 |

[1]MORWET ® EFW, manufactured by Witco, Houston, TX
[2]MORWET ® D425, manufactured by Witco, Houston, TX In this evaluation, each of the above samples is dispersed in water and sprayed onto a glass surface so as to obtain a rate of 10 mg/$M^2$ of active ingredient. For each treatment, a group of 10 German cockroaches (*Blattella germanica*) is placed on the sprayed glass surface and allowed to remain for a period of 1 hour or 6 hours. The cockroaches are then removed to clean jars and observed for mortality. Observation of mortality are made at 1, 2 and 4 days after treatment (DAT). Each treatment is replicated three times. The data are averaged and shown in Table II.

TABLE II

| | % Mortality | | | | | |
|---|---|---|---|---|---|---|
| Test | 1 DAT | | 2 DAT | | 4 DAT | |
| Sample | 1 hr. | 6 hr. | 1 hr. | 6 hr. | 1 hr. | 6 hr. |
| I-A | 30 | 20 | 30 | 25 | 35 | 35 |
| I-B | 15 | 50 | 40 | 60 | 40 | 60 |
| I-C | 30 | 50 | 35 | 65 | 40 | 70 |
| I-D | 45 | 45 | 60 | 55 | 65 | 55 |
| I-E | 85 | 95 | 95 | 95 | 100 | 95 |
| I-F | 10 | 70 | 15 | 75 | 25 | 85 |
| I-G | 60 | 95 | 90 | 95 | 95 | 100 |
| Untreated | 0 | 0 | 0 | 0 | 0 | 0 |

As can be seen from the data shown on Table II, addition of an abrasive such as calcium silicate (I-E) and/or high levels of an abrasive such as kaolin clay (I-G) significantly enhance the efficacy of the sprayable insecticidal composition of the invention. Further, it can be seen that a high level of surfactant (I-F) decreases efficacy.

EXAMPLE 2

Evaluation of the Efficacy of Sprayable Insecticidal Compositions Containing Low Levels of Surfactant and Comparative Evaluation of Insecticidal Compositions Having a Low Level of Surfactant vs. a Conventional Sprayable Insecticidal Composition The wettable powder compositions shown in Table III are prepared by combining all ingredients and milling until homogeneous.

TABLE III

| Ingredient | wt/wt % | | | | | | | | |
|---|---|---|---|---|---|---|---|---|---|
| | A | B | C | D | E | F | G | H | I |
| Chlorfenapyr | 25.1 | 25.1 | 25.1 | 25.1 | 25.1 | 25.1 | 25.1 | 25.1 | 25.1 |
| Wetting Agent[1] | 1.5 | 1.5 | 1.5 | 1.5 | 1.5 | 1.5 | 1.5 | 1.5 | 1.5 |
| Dispersing Agent[2] | 2.5 | 2.5 | 2.5 | 2.5 | 2.5 | 2.5 | 2.5 | 2.5 | 2.5 |
| Calcium Chloride | — | 3.0 | 6.0 | — | 30. | 6.0 | — | 3.0 | 6.0 |
| Calcium Silicate | — | — | — | 3.0 | 3.0 | 3.0 | 6.0 | 6.0 | 6.0 |
| Kaolin Clay | 70.9 | 67.9 | 64.9 | 67.9 | 64.9 | 61.9 | 64.9 | 61.9 | 58.9 |

[1]MORWET ® EFW, manufactured by Witco, Houston, TX
[2]MORWET ® D425, manufactured by Witco, Houston, TX A suspension concentrate formulation (2SC) containing 22.2% wt/wt of chlorfenapyr and essentially no abrasives is prepared as described in U.S. Pat. No. 5,496,845 and evaluated and compared as described hereinbelow.

In this evaluation, each of the above samples is dispersed in water and sprayed onto a glass surface so as to obtain a rate of 10 mg/$M^2$ of active ingredient. For each treatment, a group of 10 German cockroaches is placed on the sprayed glass surface for 1.25 hours and then removed and placed in clean glass jars. Observations of mortality are made daily for 4 days after treatment (DAT). Each treatment is replicated three times. The data are averaged and shown in Table IV.

TABLE IV

| Test | % Mortality | | | |
|---|---|---|---|---|
| Sample | 1 DAT | 2 DAT | 3 DAT | 4 DAT |
| III-A | 36.67 | 50.00 | 50.00 | 50.00 |
| III-B | 43.33 | 63.33 | 63.33 | 63.33 |
| III-C | 53.33 | 63.33 | 66.67 | 66.67 |
| III-D | 53.33 | 63.33 | 63.33 | 63.33 |
| III-E | 46.67 | 70.00 | 70.00 | 70.00 |
| III-F | 40.00 | 63.33 | 63.33 | 63.33 |
| III-G | 50.00 | 76.67 | 80.00 | 80.00 |
| III-H | 26.67 | 46.67 | 46.67 | 46.67 |
| III-I | 36.67 | 63.33 | 66.67 | 66.67 |
| 2SC | 10.00 | 16.67 | 16.67 | 16.67 |
| Untreated | 3.33 | 3.33 | 3.33 | 3.33 |

As can be seen from the data shown in Table IV sprayable compositions having relatively low surfactant levels in combination with high levels of abrasive give increased efficacy, with (III-E) or without (III-G) calcium chloride. Also, as can be seen from the data shown in Table IV the compositions of the invention show significantly enhanced efficacy as compared to that of a conventional sprayable insecticidal composition (2 SC).

EXAMPLE 3

Comparative Evaluation of the Efficacy of Sprayable Insecticidal Compositions of the Invention vs. a Conventional Sprayable Insecticidal Composition Composition A The wettable powder composition shown below is prepared by combining all of the ingredients and milling until homogeneous.

| Ingredient | wt/wt % |
|---|---|
| Chlorfenapyr | 25.9 |
| Wetting Agent[1] | 1.5 |
| Dispersing Agent[2] | 2.5 |
| Calcium Chloride | 3.0 |
| Calcium Silicate | 6.0 |
| Kaolin Clay | 61.1 |

[1]MORWET ® EFW,
[2]MORWET ® D425

Composition B

A suspension concentrate (2SC) composition containing 22.2% chlorfenapyr and essentially no abrasive is prepared according to U.S. Pat. No. 5,496,845 and evaluated and compared as described hereinbelow.

In this evaluation, test compositions are dispersed in water and sprayed onto a masonite (porous substrate) or stainless steel surface (non-porous substrate) so as to obtain a rate of 100 mg/$M^2$ and a rate of 200 mg/$M^2$. For each treatment, a group of 10 male German cockroaches are placed on the sprayed surface for a 1 hour period, then transferred to a clean glass jar. Observations of mortality are made at 1, 2 and 4 days after treatment (DAT). Each treatment is replicated 3 times. The data are averaged and shown in Table V.

TABLE V

| Test Composition | Surface Type | Rate (mg/$M^2$) | % Mortality | | |
|---|---|---|---|---|---|
| | | | 1 DAT | 2 DAT | 4 DAT |
| A | Masonite | 200 | 53 | 80 | 88 |
| A | Masonite | 100 | 15 | 43 | 70 |
| A | Stainless Steel | 200 | 62 | 83 | 95 |
| A | Stainless Steel | 100 | 33 | 53 | 85 |
| B | Masonite | 200 | 3 | 25 | 48 |
| B | Masonite | 100 | 8 | 15 | 25 |
| B | Stainless Steel | 200 | 3 | 25 | 63 |
| B | Stainless Steel | 100 | 8 | 13 | 53 |

As can be seen from the data shown in Table V, the sprayable insecticidal composition of the invention (A) demonstrates significantly increased efficacy on crawling insects compared to the conventional sprayable insecticidal composition (B). This increased efficacy is demonstrated for both non-porous (stainless steel) and porous (masonite) substrates.

EXAMPLE 4

Comparative Evaluation of the Efficacy of Sprayable Insecticidal Compositions of the Invention on a Variety of Cockroach Species vs. that of a Conventional Sprayable Insecticidal Composition Using essentially the same procedure described hereinabove for Example 3 and employing a vinyl surface (very highly porous) sprayed with Test Compositions A and B as described n Example 3, at a rate of 100 mg/M$^2$, three species of cockroaches were exposed for 1 hour, then placed in clean jars. Each treatment is replicated five times. Observations of mortality were made at 1 and 2 days after treatment. The data are averaged and shown in Table VI.

TABLE VI

| Insect Species Used | |
|---|---|
| Common Name | Scientific Name |
| American Cockroach | *Periplaneta americana* |
| Smokybrown Cockroach | *Periplaneta fuliginosa* |
| Oriental Cockroach | *Blatta orientails* |

| Test Composition | Cockroach Species | % Mortality | |
|---|---|---|---|
| | | 1 DAT | 2 DAT |
| A | American | 100 | 100 |
| A | Smokybrown | 68 | 100 |
| A | Oriental | 88 | 100 |
| B | American | 0 | 0 |
| B | Smokybrown | 0 | 7 |
| B | Oriental | 0 | 47 |

As can be seen from the data in Table VI the insecticidal sprayable composition of the invention demonstrates significantly increased efficacy as compared to that of the conventional sprayable composition across a variety of species of cockroaches.

EXAMPLE 5

Comparative Evaluation of the Efficacy of Sprayable Insecticidal Compositions of the Invention when Applied Directly to the Target Species vs. that of a Conventional Sprayable Insecticidal Composition In this evaluation, dilutions of Test Composition A and B as described in Example 3 hereinabove are employed. Cockroach harborages are fashioned and infested with a group of mixed adult German cockroaches (5 males and 5 females), then the diluted Test Compositions are sprayed into the infested harborages. Each treatment is replicated 8 times. Observation of mortality are made 1 hour, 1 day and 4 days after treatment. The data are averaged and shown in Table VII.

TABLE VII

| Test Composition | Concentration (wt/wt % av) | % Mortality | | |
|---|---|---|---|---|
| | | 1 hr. | 1 day | 4 days |
| A | 0.50 | 38 | 76 | 99 |
| A | 0.25 | 25 | 81 | 98 |
| B | 0.50 | 15 | 50 | 79 |
| B | 0.25 | 10 | 50 | 71 |

As can be seen from the data in Table VII, the sprayable insecticidal composition of the invention (A) demonstrates significantly increased efficacy upon direct contact with the insect than the conventional sprayable composition (B).

I claim:

1. A non-aqueous sprayable insecticidal composition which comprises from 10 to 70% by weight of at least one insecticide;

from about 3% to about 9% by weight of an abrasive selected from the group consisting of alkali metal silicates and alkaline earth metal silicates;

from about 2% to about 15% by weight of a surfactant;

from 25 to 75% by weight of a solid inert carrier; and an effective amount of an agent to inhibit the formation of a film, wherein the weight percentages are based on the total weight of the non-aqueous sprayable insecticidal composition, and wherein the agent to inhibit the formation of a film is an alkali metal halide or an alkaline earth metal halide.

2. The composition defined in claim 1, wherein the agent to inhibit the formation of a film is present in from 1 to 6% by weight of the composition.

3. The composition defined in claim 1, wherein the inert carrier is kaolin clay.

4. The composition defined in claim 1, wherein the abrasive is calcium silicate.

5. The composition defined in claim 4, wherein the calcium silicate is present in from 5 to 7% by weight of the composition.

6. The composition defined in claim 1, wherein the surfactant is present in form 2 to 7% by weight of the composition.

7. The composition defined in claim 1, which comprises from 10 to 30% by weight of the at least one insecticide;

from about 2% to about 7% by weight of the surfactant; and from 55 to 75% by weight of the solid inert carrier.

8. The composition defined in claim 7, wherein the insecticide is selected from insecticides effective against crawling insect pests.

9. The composition defined in claim 8, wherein the crawling insect pests are selected from the group consisting of cockroaches, ants, crickets, silverfish, earwigs, flour beetles, termites and wood-boring beetles.

10. The composition defined in claim 1, which comprises from 10 to 30% by weight of the at least one insecticide;

from about 2% to about 7% by weight of the surfactant;

from 55 to 75% by weight of the solid inert carrier; and from 1 to 6% by weight of the agent to inhibit the formation of a film.

11. The composition defined in claim 10, wherein the insecticide is selected from insecticides effective against crawling insect pests.

12. The composition defined in claim 11, wherein the crawling insect pests are selected from the group consisting of cockroaches, ants, crickets, silverfish, earwig, flour beetles, termites and wood-boring beetles.

13. The composition defined in claim 1, which comprises from 10 to 30% by weight of the at least one insecticide;

from about 3% to about 9% by weight of calcium silicate;

from about 2% to about 7% by weight of the surfactant;

from 55 to 75% by weight of kaolin clay; and from 1 to 6% by weight of calcium chloride.

14. The composition defined in claim 13, wherein the insecticide is selected from insecticides effective against crawling insect pests.

15. The composition defined in claim 14, wherein the crawling insect pests are selected from the group consisting of cockroaches, ants, crickets, silverfish, earwig, flour beetles, termites and wood-boring beetles.

16. The composition defined in claim 1, wherein the insecticide is selected from insecticides effective against crawling insect pests.

17. The composition defined in claim 1, wherein the crawling insect pests are selected from the group consisting of cockroaches, ants, crickets, silverfish, earwigs, flour beetles, termites and wood-boring beetles.

* * * * *

UNITED STATES PATENT AND TRADEMARK OFFICE
CERTIFICATE OF CORRECTION

PATENT NO.        : 6,869,613 B2                           Page 1 of 1
APPLICATION NO.   : 09/282857
DATED             : March 22, 2005
INVENTOR(S)       : Kimler et al.

It is certified that error appears in the above-identified patent and that said Letters Patent is hereby corrected as shown below:

<u>Title page,</u>
Item [56], References Cited, FOREIGN PATENT DOCUMENTS, add the following:
-- WO   96 05721 A    2/1998
   WO   94 27434 A    12/1994
   GB   2 314 774 A   2/1998
   EP   0 821 876 A   2/1998
   JP   58-124703-A   1/1982 --.

Signed and Sealed this

Twentieth Day of June, 2006

JON W. DUDAS
*Director of the United States Patent and Trademark Office*